US009115103B2

(12) United States Patent
Van Westrenen

(10) Patent No.: US 9,115,103 B2
(45) Date of Patent: Aug. 25, 2015

(54) PROCESS FOR REMOVING OXYGENATE FROM AN OLEFIN STREAM

(71) Applicant: Shell Oil Company, Houston, TX (US)

(72) Inventor: Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 14/136,222

(22) Filed: Dec. 20, 2013

(65) Prior Publication Data

US 2014/0187806 A1   Jul. 3, 2014

(30) Foreign Application Priority Data

Dec. 28, 2012 (EP) .................................. 12199704

(51) Int. Cl.
| | | |
|---|---|---|
| C07C 1/00 | (2006.01) | |
| C07D 301/02 | (2006.01) | |
| C07C 7/08 | (2006.01) | |
| C07C 41/42 | (2006.01) | |
| C07C 1/20 | (2006.01) | |

(52) U.S. Cl.
CPC ............... *C07D 301/02* (2013.01); *C07C 1/20* (2013.01); *C07C 7/08* (2013.01); *C07C 41/42* (2013.01); *C07C 2529/70* (2013.01)

(58) Field of Classification Search
CPC ............ C07C 7/08; C07C 4/42; C07C 43/04; C07C 1/20; C07C 2529/70; C07C 11/06; C07C 41/42; C07C 43/043; C07D 301/02
USPC ............................ 549/523; 585/324, 329, 864
See application file for complete search history.

(56) References Cited

U.S. PATENT DOCUMENTS

| 4,567,029 A | 1/1986 | Wilson et al. |
|---|---|---|
| 7,002,050 B2 | 2/2006 | Santiago Fernandez et al. |
| 7,132,580 B1 | 11/2006 | Senetar |
| 2003/0045644 A1 | 3/2003 | Mougin |
| 2007/0155999 A1 | 7/2007 | Pujado et al. |
| 2007/0203380 A1 | 8/2007 | Vora et al. |
| 2009/0223870 A1 | 9/2009 | Birke et al. |

FOREIGN PATENT DOCUMENTS

| WO | 03020678 | 3/2003 |
|---|---|---|
| WO | 2006020083 | 2/2006 |

OTHER PUBLICATIONS

Reichardt, Christian, Solvents and Solvent Effects in Organic Chemistry, 2003, Verlag GMbH & Co., 3rd ed., p. 1-37.*
Nowowiejski et al., An overview of oxygenates in olefins units in relation to corrosion, fouling, product specifications, and safety, Presentation at American Institute of Chemical Engineers 2003 Spring National Meeting, New Orleans, USA, in particular page 16.

* cited by examiner

*Primary Examiner* — T. Victor Oh

(57) ABSTRACT

The present invention relates to a process for producing an olefinic product, comprising (a) preparing a reaction product by converting an oxygenate-comprising feedstock in an oxygenate to olefin process, the reaction product comprising at least C2+ olefins and DME, (b) separating at least part of the reaction product by means of extractive distillation using a butanol solvent into: (i) a first fraction comprising C3− olefins and butanol; and (ii) a second fraction comprising C4+ olefins, DME and butanol; (c) separating the first fraction into: (iii) a C3− olefinic product; and (iv) a third fraction comprising butanol; (d) separating the second fraction into: (v) a DME-comprising C4-C5 olefinic product; and (vi) a fourth fraction comprising butanol and C6+ olefins, wherein at least part of the third and/or fourth fraction are recycled to step (b) together with or as part of the butanol solvent.

12 Claims, 2 Drawing Sheets

PROCESS FOR REMOVING OXYGENATE FROM AN OLEFIN STREAM

This application claims the benefit of European Application No. 12199704.3 filed Dec. 28, 2012, which is incorporated herein by reference.

FIELD OF THE INVENTION

The present invention relates to a process for removing oxygenate from an olefin stream.

BACKGROUND OF THE INVENTION

Conventionally, ethylene and propylene are produced via steam cracking of paraffinic feedstocks including ethane, propane, naphtha and hydrowax. An alternative route to ethylene and propylene is an oxygenate-to-olefin (OTO) process. Interest in OTO processes for producing ethylene and propylene is growing in view of the increasing availability of natural gas. Methane in the natural gas can be converted into for instance methanol or dimethylether (DME), both of which are suitable feedstocks for an OTO process.

In an OTO process, an oxygenate such as methanol is provided to a reaction zone of a reactor comprising a suitable conversion catalyst whereby the oxygenate is converted to ethylene and propylene. In addition to the desired ethylene and propylene, a substantial part of the oxygenate, such as methanol, is converted to higher hydrocarbons including C4+ olefins and paraffins. The effluent from the reactor comprising the olefins, any unreacted oxygenates such as alcohols or ethers, particularly methanol and dimethylether and other reaction products such as water may then be treated to provide separate component streams. Unreacted oxygenates can be separated from the reaction effluent, for instance by contacting with a cooled aqueous stream in a quench zone. In order to increase the ethylene and propylene yield of the process, the C4+ olefins may be recycled to the reaction zone or alternatively further cracked in a dedicated olefin cracking zone to produce further ethylene and propylene.

In patent application WO 03/020678, a process for the removal of dimethylether from an olefinic stream is disclosed. In the process of WO 03/020678, the olefinic stream comprising dimethylether is first separated into a first stream comprising dimethylether and lighter boiling point compounds and a second stream comprising C4+ olefin and higher boiling point hydrocarbons. The stream comprising dimethylether subjected to an extractive distillation using an extraction solvent to remove at least part of the dimethylether. Methanol may for instance be used as a solvent.

A similar process is described in U.S. patent application Ser. No. 20090223870, a liquid phase containing hydrocarbons and oxygenates is charged to a separation vessel and separated into a light gaseous fraction and a heavier C4+ fraction. The light gaseous fraction together with a gaseous stream is subjected to an extractive distillation with an extraction solvent, which dissolves the oxygenates, to remove at least part of the oxygenates from the combined gaseous stream. The preferred solvents are methanol or NMP.

Where a gaseous stream is contacted with a liquid solvent, inevitably part of the liquid solvent will evaporate, due to its vapour pressure. As a result the combined gaseous stream is contaminated with the solvent.

Although NMP has the advantage that it has a low vapour pressure, i.e. as much as 100 times lower than methanol, a disadvantage of using NMP is that it is typically not readily available at the process site and thus must be provided externally.

Methanol may be more readily available to use a solvent, however, due to the high vapour pressure of the methanol, the light olefin rich, dimethylether lean overhead vapour stream will comprise substantial amounts of methanol as a contaminant. When methanol is diluted in a non-polar environment, such as the light olefin rich overhead vapour stream, its properties are no longer determined by its ability to form hydrogen bonds with other polar compounds. Rather, the methanol properties, i.e. its vapour/liquid equilibrium properties, are determined based on its molecular weight. Consequently, methanol when diluted in a non-polar environment behaves similar to a C3 hydrocarbon. In the subsequent treatment of the light olefin rich, dimethylether lean overhead vapour stream to isolate ethylene and propylene product streams such diluted methanol will accumulate in the ethylene and propylene product streams. Methanol-contaminated ethylene and propylene is less suitable as a feedstock for preparing olefin derivatives such as polyethylene or polypropylene. Removing, the diluted methanol from the ethylene and propylene product is difficult and energy consuming.

U.S. Pat. No. 7,132,580 discloses a methanol to olefin catalytic conversion process including the selective recovery and recycle of dimethylether and methanol from the effluent stream of the reactor. After the reactor effluent stream is charged to a quench zone, the resulting cooled overhead vapour stream can be compressed. The compressed stream can then be passed to a separation zone to recover a vapour stream which is then passed to a dimethylether absorption zone. The vapour stream is contacted with a dimethylether selective solvent containing methanol at scrubbing conditions effective to produce a liquid solvent bottom stream containing methanol, dimethylether, water and substantial and undesired amounts of ethylene and propylene and a light olefin rich, dimethylether lean overhead vapour stream containing methanol.

The liquid solvent bottom stream further treated to remove a substantial portion of ethylene and propylene contained in the stream. According to U.S. Pat. No. 7,132,580, the use of a dimethylether selective solvent containing methanol in the dimethylether absorption zone necessarily results in a vapour stream that is saturated with methanol at the conditions prevailing at the top of the dimethylether absorption zone. As mentioned above, due to the properties of the diluted methanol in the light olefin rich, dimethylether lean overhead vapour stream, part of the methanol will end up as a contaminant in the ethylene and propylene product streams. Consequently, unless additional steps are taken to rigorously remove methanol from the light olefin rich, dimethylether lean overhead vapour stream, the light olefin product may be contaminated with methanol. The process of U.S. Pat. No. 7,132,580 therefore requires a secondary methanol absorption zone in which the light olefin rich, overhead vapour stream is contacted with an aqueous solvent at scrubbing conditions to remove methanol to produce a dimethylether-lean and methanol-lean overhead vapour product stream comprising ethylene and propylene and a bottom stream containing methanol and aqueous solvent. Nowowiejski et al. (Nowowiejski et al., An overview of oxygenates in olefins units in relation to corrosion, fouling, product specifications, and safety, Presentation at American Institute of Chemical Engineers 2003 Spring National Meeting, New Orleans, USA, in particular page 16) disclose the risk of methanol breakthrough in a C3 splitter even where the feed to the C3 splitter only contains small amounts of methanol. According to Nowowiejski et al., methanol, entering a C3 splitter producing a polymer grade propylene product, will concentrate in the C3 splitter around the 90 to 95 percent propylene zone in the C3 splitter. If methanol levels in the C3 splitter build up over time, a minor upset or change in operating conditions may result in off-spec methanol contaminated propylene product.

A need exists to provide an improved process for the removal of oxygenates from hydrocarbon streams, in particular hydrocarbons streams containing ethylene and propylene. Preferably, a process that mitigates the contamination of the light olefin rich overhead vapour stream with additional methanol.

SUMMARY OF THE INVENTION

It has now been found that the problems encountered with the prior art processes can be solved by utilising a liquid solvent comprising a butanol to absorb oxygenates present in an olefin stream. In contrast to the process of U.S. Pat. No. 7,132,580, the use of such a liquid solvent comprising a butanol significantly reduces the energy consumption of any secondary solvent absorption zone to remove solvent from the ethylene and/or propylene product.

Accordingly, the present invention provides an integrated process in which the butanol and can be prepared from the olefin product of an OTO process. As such the need to provide an additional external solvent is removed as the solvent may be prepared in-situ.

The process according to the present invention does not require hold up of valuable methanol feedstock to be used for other purposes.

Accordingly, the present invention provides a process for producing an olefinic product, comprising:
 a) preparing an reaction product by converting an oxygenate-comprising feedstock in an oxygenate to olefin process, the reaction product comprising at least C2+ olefins and DME
 b) separating at least part of the reaction product by means of extractive distillation using a butanol solvent into:
  a first fraction comprising C3− olefins and butanol; and
  a second fraction comprising C4+ olefins, DME and butanol;
 c) separating the first fraction into:
  a C3− olefinic product; and
  a third fraction comprising butanol;
 d) separating the second fraction into:
  a DME-comprising C4-C5 olefinic product; and
  a fourth fraction comprising butanol and C6+ olefins,
wherein at least part of the third and/or fourth fraction are recycled to step (b) together with or as part of the butanol solvent.

Figure 1:
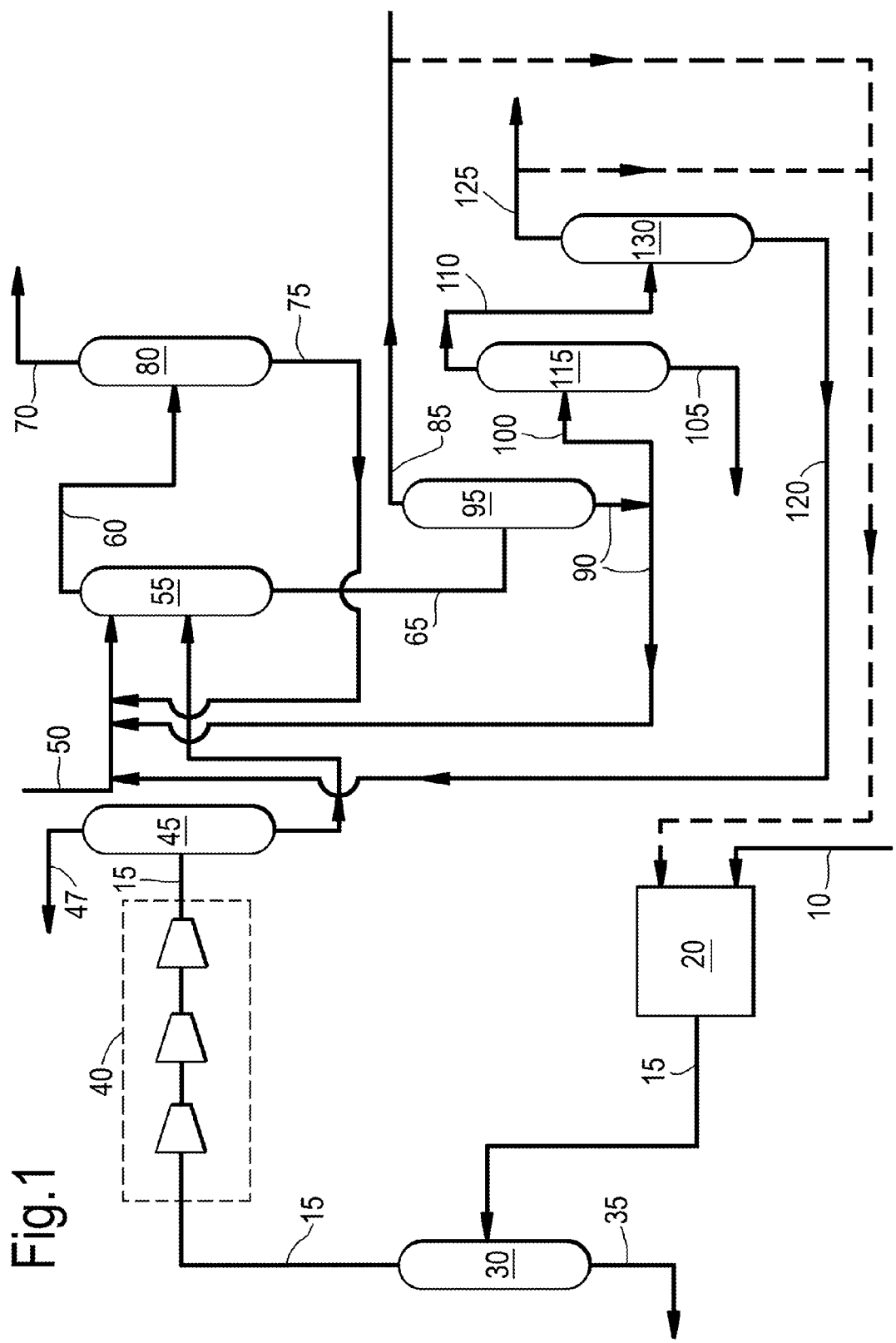
FIG. 1. depicts a diagrammatic scheme of one embodiment of a process for removing oxygenate from an olefin stream comprising oxygenate described herein.

While the invention is susceptible to various modifications and alternative forms, specific embodiments thereof are shown by way of example in the drawings and will herein be described in detail. It should be understood that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The process described herein is a process for removing dimethylether (DME) from a reaction product obtained from an oxygenate-to-olefin process. The process according to the invention is advantageous because the reaction product is treated with a butanol solvent, rather than the dimethylether selective solvent containing methanol described in U.S. Pat. No. 7,132,580. Unlike methanol, the butanol solvent described herein has a low volatility, also in dilute mixtures, in particular dilute non-polar hydrocarbon comprising mixtures, such that the butanol solvent described herein is separated from the light hydrocarbons more easily and requiring significantly less energy.

Reference herein to a butanol is to 1-butanol, 2-butanol, 2-methyl-1-propanol (isobutanol), 2-methyl-2-propanol (tert-butanol).

Reference herein to an olefin stream is to a stream comprising at least olefins.

Reference herein to an olefinic stream is to a stream comprising at least olefins.

Reference herein to a spent solvent is to a solvent that has been in contact with an olefin stream comprising oxygenate.

Reference herein below to the butanol solvent or to the solvent according to the invention is to asolvent comprising one or more of 1-butanol, 2-butanol, 2-methyl-1-propanol (isobutanol), 2-methyl-2-propanol (tert-butanol).

The process according to the invention is now described in more detail with reference to FIG. 1. In the process described herein, an oxygenate-comprising feedstock (10) is converted to a reaction product (15) in an oxygenate-to-olefins process (OTO), i.e. step (a). Typically, the OTO process is operated in an OTO reactor (20), wherein the oxygenate-comprising feedstock is contacted with a catalyst. OTO processes are well known in the art and are able to convert oxygenates, like methanol or DME, to olefins, in particular ethylene and propylene. The reaction product of the OTO process comprises C2+ olefins and DME. The C2+ olefins herein comprise ethylene (C2), propylene (C3), butylene (C4) pentene (C5), hexene (C6), including benzene, and optionally higher olefins. The C4 olefins may comprise 1-butene, 2-butene and isobutene. The reaction product preferably comprises at least 25 wt % olefin, more preferably 50 wt % olefin, even more preferably at least 60 wt % olefin, and still more preferably at least 70 wt % olefin, based on the hydrocarbon content of the reaction product. It is particularly preferred that reaction product comprises at least 25 wt % ethylene and/or propylene, more preferably 50 wt % ethylene and/or propylene, even more preferably at least 60 wt % of ethylene and/or propylene, and still even more preferably at least about 70 wt % of ethylene and/or propylene, based on the olefins in the reaction product. In a preferred embodiment the olefin stream comprising oxygenates comprises at least 50 wt % propylene, even more preferably at least 60 wt % of propylene, and still even more preferably at least about 70 wt % of propylene, based on the olefins in the reaction product.

The reaction product also comprises DME. Where DME was part of the oxygenate-comprising feedstock to the OTO process, the DME may at least in part be unreacted feedstock. DME is however also formed as a reaction product in the OTO process irrespective of the choice of oxygenate in the feedstock. Preferably, the reaction product comprise in the range of from 1 ppmv no more than 10 vol %, more preferably of from 100 ppmv to 5 vol %, even more preferably of from 100 ppmv to 1 vol %, still more preferably of from 100 ppmv to 0.5 vol %, even still more preferably of from 100 ppmv to 0.1 vol % of DME, based on the hydrocarbon content of the reaction product. DME is an undesired compound in the reaction product as it has the tendency to accumulate in the C3 olefin-comprising fraction during a subsequent fractionation of the reaction product. In particular where produced propylene in the reaction product is to be used for the production of polypropylene or propylene oxide, the presence of DME is unwanted. Other compounds in the reaction product may include, but are not limited to, water (steam), paraffins, methane, $H_2$, CO, and $CO_2$.

In the process according to the present invention, the reaction product is treated with a butanol solvent to remove at least part of the DME, i.e. step (b). Preferably, prior to treating the reaction product with the butanol solvent, the reaction product is treated to remove at least part of the water (steam) in the reaction product. Steam is used as a diluent in many OTO processes, while water is also one of the reaction products. Water (steam) is typically removed using a quench. The reaction product obtained from the OTO process may be provided to a quench tower (30) and may be quenched to condensate at least part of the steam in the reaction product. After removal of at least part of the condensed water (35) in the quench tower (30), the reaction product is preferably compressed. Preferably, the reaction product is provided to a compression section (40) where the reaction product is compressed in one or more stages of a compressor train or the compression section. Preferably, in the final stages of the compression of the reaction product, liquid hydrocarbons condense out from the reaction product. This condensate may subsequently be stripped in a condensate stripper to remove any entrained C3 and lighter hydrocarbons. These C3 and lighter hydrocarbons may at some stage be re-combined with at least part of the reaction product.

In one embodiment, the reaction product, prior to treating the reaction product with the butanol solvent, is treated to remove one or more of ethylene, ethane, methane, $H_2$, CO and $CO_2$. Such a separation of the reaction product may include providing the reaction product to a de-ethaniser column (45). Optionally, such a separation may include proving the reaction product to a de-methaniser column to remove at least methane, $H_2$, CO and $CO_2$, and subsequently providing the remaining reaction product to the de-ethaniser column to remove at least ethylene and ethane. De-methaniser and/or de-ethaniser separation is well known in the art. The reaction product, after separation of the C2− product (47), is also referred to as the C3+ reaction product.

In the process according to the invention, at least part of the reaction product is separated by means of extractive distillation using a butanol solvent (50) in a extractive distillation unit (55). With respect to the non-oxygenate hydrocarbons, the extractive distillation conditions are chosen such that the top product consist predominantly of C3+ products. As such, the extractive distillation is operates to act as a de-propeniser.

Preferably, where the butanol solvent comprises tert-butanol or isobutanol. Although, isobutanol has properties comparable to tert-butanol and may also be used to absorb DME from the reaction product, the present invention preferably uses tert-butanol rather than isobutanol for the reason that the tert-butanol may be produced from products obtained from an oxygenate to olefins process, as described herein below.

Preferably, the butanol solvent comprises in the range of from 75 to 100 wt % of butanol, based on the weight of the butanol solvent, excluding any absorbed DME. Even more preferably, in the range of from 90 to 100 w %, still more preferably of 97 to 100 wt %, of butanol, based on the weight of the butanol solvent, excluding any absorbed DME. The most preferred butanol being isobutanol and tert-butanol, in particular tert-butanol.

A highly preferred butanol solvent is a solvent comprising tertbutanol as the only butanol. A particular advantage of the use of tert-butanol solvent is that it can be produced solely from reaction by-products, where processes using methanol or methanol derived solvents necessitate diverting part of the methanol feedstock to remove oxygenates from products streams, as described herein below.

The butanol solvent may however, comprise small amounts of other components, preferably components that have a vapour pressure similar to butanols, such as other C3+ alcohols. Such small amounts of other components may have been introduced for instance by re-using at least part of the spent butanol solvent, optionally after treating the spent butanol solvent to remove absorbed DME.

The reaction product is contacted with the butanol solvent in an extractive distillation process. The extractive distillation process may comprise one or more extraction and/or separation steps. The extractive distillation process may take place in an extractive distillation vessel or column, which can be of conventional design. Preferably a packed distillation column is used.

Preferably, reaction product is treated with the butanol solvent at a pressure of from 2.5 to 350 bara. More preferred operating pressure ranges are of from 5 to 60 bara even more preferably 10 to 50 bara. Preferably, reaction product is treated with the butanol solvent at a temperature in the range of from 0 to 60° C., preferably of from 25 to 60° C., where the solvent comprises tert-butanol as pure tert-butanol is a solid at temperatures under 25° C.

As the pressure in the extractive distillation vessel increases, the more dimethylether may be removed from the olefin stream.

An extractive distillation process is preferred, for instance over a wash column, as the combination of energy input and solvent addition improves the separation between the components, allowing for an effective removal of even very low concentrations of oxygenate present in the olefin stream comprising oxygenates and reducing the losses of valuable components in the solvent.

The extractive distillation process is preferably operated below the boiling point of the butanol solvent and its individual components, and above the boiling point of at least part of the components in reaction product at the operating conditions prevailing in the extractive distillation column. It is preferred to operate the process such that the formation of two liquid phases in the column is prevented. As the butanol solvent travels through the distillation column, DME is absorbed into the butanol solvent and removed along with the butanol solvent at the bottom of the extractive distillation column. Preferably, the temperature is maintained below a temperature at which the butanol in the solvent start to decompose or vaporise. The extractive distillation process herein may comprise one or more stages and one or more columns, optionally with intermediate reheating.

During the extractive distillation the reaction product is separated into at least a first fraction (60) comprising C3− olefins and butanol, and a second fraction (65) comprising C4+ olefins, DME and butanol.

The first fraction comprises C3− olefins. Reference herein to C3− olefins is to propylene and ethylene. Where the reaction product was previously treated to separate the ethylene from the reaction product, the C3− fraction will predominantly comprise propylene and propane.

Preferably, the first fraction contains less than 100 ppmv, more preferably less than 75 ppmv, even more preferably less than 50 ppmv of DME, based on the propylene in the first fraction.

The first fraction will also comprise some of the butanol solvent.

The second fraction comprises C4+ olefins. Reference herein to C4+ olefins is to olefins having a carbon number of 4 or higher. Preferably, the C4+ olefins include butylene, pentene and hexene, preferably including at least benzene. The second fraction will also comprise butanol and DME, which was absorbed by the butanol solvent.

The extractive distillation is operated to allow the C3– olefins in the reaction product to be retrieved as the first fraction as the top effluent from the extractive distillation column, while the spent butanol solvent comprising at least part, preferably a majority, of the DME, originally comprised in the reaction product, is retrieved as part of the second fraction as a bottom stream. Some of the butanol solvent may however be carried over the top as part of the first fraction. Therefore, the first fraction is further treated to remove at least part of the butanol solvent. Therefore, in the process according to the invention, the first fraction is subsequently separated to remove at least part of the butanol from the first fraction. The first fraction is separated into a C3– olefinic product (70), comprising propylene and optionally propane, ethane, ethylene, $H_2$, CO, and $CO_2$, and a third fraction (75) comprising butanol. The first fraction may be separated using a distillation column (80), retrieving the third fraction as the bottom effluent. Optionally, C3– olefinic product (70) is subsequently recompressed. It is an advantage of the present invention that while the butanols act as solvent for DME in the reaction product, they do not form azeotropic mixtures with light (C2 and C3) hydrocarbons, reducing the complexity of the subsequent separation of the carried over liquid solvent in the first fraction from the olefins to produce the C3– olefinic product.

It is a particular advantage of the present invention that the butanols in the butanol solvent have boiling temperatures that are significantly higher than that of the C3 olefins in the olefin stream. This distinguishes the process of the present invention from prior art processes using methanol-based solvents to extract DME, where the methanol diluted in a non-polar hydrocarbon phase has a boiling point similar to propylene. The higher boiling temperature of the butanol solvent according to the present invention, also when diluted in a non-polar hydrocarbon phase, allow for a removal of any carried over butanol at a much lower energy consumption that would have been required when the solvent used was a methanol-based solvent.

The majority of the butanol solvent is retrieved as part of the second fraction. Preferably, the butanol solvent is retrieved from the second fraction to be reused in the extractive distillation. Therefore, in the process according to the invention, the second fraction is subsequently separated to retrieve at least part of the butanol from the second fraction. The second fraction is separated into a DME-comprising C4-C5 olefinic product (85); and a fourth fraction (90) comprising butanol and C6+ olefins. The second fraction may be separated using a distillation column (95), retrieving the fourth fraction as the bottom effluent.

In the process according to the invention, at least part of the third and/or fourth fraction is recycled to the extractive distillation of step (b) together with or as part of the butanol solvent. Preferably, at least part of the fourth fraction is recycled to the extractive distillation of step (b) as this fraction will contain the larger part of the butanol provided as part of the butanol solvent to the process.

At least part of the fourth fraction may recycled to the extractive distillation. To prevent a build up of 6+ olefins, and optionally other compounds other than butanol, in such a recycle, part of the fourth fraction will need to be withdrawn and used for other purposes. Actually, it may be preferred to separate, at least part of, the fourth fraction into a C7+ olefinic product (105), and a fifth fraction (110) comprising C6 olefins and butanol. At least at least part of the fifth fraction may preferably be recycled to the extractive distilation in step (b) together with or as part of the butanol solvent. The at least part of the fourth fraction (100) may be separated using a distillation column (115), retrieving the fifth fraction as the top effluent. Preferably, the fifth fraction is further separated into a sixth fraction (120) comprising butanol, and a seventh fraction (125) comprising C6 olefins and butanol. At least part of the sixth fraction may be recycled to the extractive distillation of step (b) together with or as part of the butanol solvent. The fifth fraction may be separated using a distillation column (130), retrieving the sixth fraction as the bottom effluent.

The C7+ olefinic product preferably comprises one or more of toluene and xylenes, which may be isolated from the C7+ olefinic product. Toluene and xylenes are valuable product and may be used elsewhere. At least part and preferably all of the seventh fraction, optionally even the fifth fraction, is preferably recycled back to the OTO process together with or as part of the oxygenate comprising feedstock in step (a). The C6 olefins in the fifth and seventh fraction will comprise benzene. Actually, a substantial part of those C6 olefins will be benzene molecules. When benzene is fed to a OTO process, it may be alkylated to form further toluene and xylenes, which can be isolated and retrieved as described herein above.

Butanol may suitably be provided to an OTO process. It is a particular advantage of the present process that the butanol solvent itself can be used as a feedstock to an OTO process. Therefore, in a further embodiment, at least a portion of the spent butanol solvent may be passed to the oxygenate reaction zone together with or a part of the oxygenate feedstock. When the spent liquid solvent is recycled to the OTO process together with or as part of the oxygenate feedstock it may be converted to additional ethylene and propylene.

As such it may be preferred to provide at least part of any one or more of the butanol-comprising fractions back to the OTO process in step (a), i.e. as long as at least part of the first fraction retrieved as the C3– olefinic product.

The DME-comprising C4-C5 olefinic product comprises butylenes. As mention above, butylene will include isobutene. Preferably, the DME-comprising C4-C5 olefinic product comprises isobutene and at least part of the butanol solvent is produced by converting such isobutene with water to tert-butanol. Due to the significant difference in boiling point between tert-butanol and DME there is no need to first separate the isobutene from the DME-comprising C4-C5 olefinic product. The tert-butanol may be separated from the DME-comprising C4-C5 olefinic product following the reaction of isobutene to tert-butanol.

The isobutene may be used to prepare tert-butanol by reacting the isobutene with water over an acid catalyst. Water is readily available as a by-product of the OTO process. The reaction of isobutene with water can be carried out in the presence of an acidic catalyst, such as an acidic ion exchange resin, preferably Amberlyst 15. The reaction conditions of these to processes are well known in the art and do not need any further explication herein. Reference is made to for instance US7002050B2, for processes and process conditions for the catalytic hydration of isobutene to tert-butanol.

As mentioned above, it is a particular advantage of the process according to the present invention that the solvent may be prepared from components provided to or products provided by an OTO process.

The thus produced tert-butanol may be passed to extractive distillation of step (b) as part of the butanol solvent. Preferably, the tert-butanol is treated to remove any water prior to being passed to the extractive distillation of step (b).

An advantage of using the butanol solvent according to the present invention is that the butanol has a lower vapour pressure than methanol in particular in diluted form. As a result, the butanol is not transported to the first fraction to the extent methanol would, i.e. under equal conditions, however even more importantly, any butanol solvent that is transported to the first fraction may removed from the C3− olefinic product at significantly less energy cost than methanol and without having to accept accumulation of solvent in the C3− olefin product or any ethylene and or propylene fractions in a final product slate. Rather, these solvents are preferably directed to higher boiling fractions.

Where tert-butanol is used as, part of, the butanol solvent, it must be realised that tert-butanol is a solid below 25° C. and 1 bara, therefore in order to use tert-butanol as part of the butanol solvent the temperature at which the reaction product is treated must be higher than 25° C., in case the butanol solvent is pure tert-butanol.

As mentioned herein above, in the process according to the invention an oxygenate feedstock is converted in an oxygenate-to-olefin process or OTO process to produce the reaction product. In an OTO process, oxygenates, preferably oxygenates such as methanol and dimethylether, are converted over a molecular sieve catalyst to at least ethylene and propylene.

OTO process are well known in the art and have for instance been described in WO A 2006/020083. Processes integrating the production of oxygenates from synthesis gas and their conversion to light olefins are described in US20070203380A1 and US20070155999A1.

The oxygenate used in an oxygenate feedstock provided to the OTO process is preferably an oxygenate which comprises at least one oxygen-bonded alkyl group. The alkyl group preferably is a C1-C5 alkyl group. Preferably, the oxygenate is methanol or dimethylether, or a mixture thereof.

A diluent, such as water or steam, may also be provided to the OTO process together with or as part of the oxygenate feedstock. Preferably, in addition to the oxygenate and diluent, an olefinic co-feed is provided along with and/or as part of the oxygenate feedstock. The olefinic co-feed preferably comprises C4+ olefins i.e. C4 and higher olefins, more preferably C4 and C5 olefins. Preferably, at least part of the olefinic co-feed, during normal operation, is formed by a recycle stream of a C4+ hydrocarbon fraction from the OTO reaction effluent, i.e. the olefin stream obtained from the OTO process. In order to maximize production of ethylene and propylene, it is desirable to maximize the recycle of C4 olefins in the effluent of the OTO process as these olefins are converted to further ethylene and propylene. Where reference is made to an OTO process, this is to process that produces significant amounts of ethylene and propylene by converting at least part of the feedstock.

Catalysts suitable for converting the oxygenate feedstock comprise one or more molecular sieves. Such molecular sieve-comprising catalysts typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieves preferably have a molecular framework of one, preferably two or more corner-sharing tetrahedral units, more preferably, two or more [SiO4], [AlO4] and/or [PO4] tetrahedral units. These silicon, aluminum and/or phosphorus based molecular sieves and metal containing silicon, aluminum and/or phosphorus based molecular sieves have been described in detail in numerous publications including for example, U.S. Pat. No. 4,567,029. In a preferred embodiment, the molecular sieves have 8-, 10- or 12-ring structures and an average pore size in the range of from about 3 Å to 15 Å. Suitable molecular sieves are silicoaluminophosphates (SAPO), such as SAPO-17, -18, 34, -35, -44, but also SAPO-5, -8, -11, -20, -31, -36, 37, -40, -41, -42, -47 and -56; aluminophosphates (AlPO) and metal substituted (silico)aluminophosphates (MeAlPO), wherein the Me in MeAlPO refers to a substituted metal atom, including metal selected from one of Group IA, IIA, IB, IIIB, IVB, VB, VIB, VIIB, VIIIB and Lanthanides of the Periodic Table of Elements. Preferably Me is selected from one of the group consisting of Co, Cr, Cu, Fe, Ga, Ge, Mg, Mn, Ni, Sn, Ti, Zn and Zr.

Alternatively, the conversion of the oxygenate feedstock may be accomplished by the use of an aluminosilicate-comprising catalyst, in particular a zeolite-comprising catalyst. Suitable catalysts include those containing a zeolite of the ZSM group, in particular of the MFI type, such as ZSM-5, the MTT type, such as ZSM-23, the TON type, such as ZSM-22, the MEL type, such as ZSM-11, and the FER type. Other suitable zeolites are for example zeolites of the STF-type, such as SSZ-35, the SFF type, such as SSZ-44 and the EU-2 type, such as ZSM-48.

Aluminosilicate-comprising catalyst, and in particular zeolite-comprising catalyst are preferred when an olefinic co-feed is fed to the oxygenate conversion zone together with oxygenate, for increased production of ethylene and propylene.

Preferred catalysts for OTO processes comprise SAPO, MEL and/or MFI type molecular sieves, whereby the latter two are zeolite molecular sieves. More preferred catalyst comprise SAPO-34, ZSM-11 and/or ZSM-5 type molecular sieves. Even more preferred catalysts for OTO processes comprise MEL and/or MFI type molecular sieves, still more preferred catalyst comprise ZSM-11 and/or ZSM-5 type molecular sieves. A preferred MFI-type zeolite for the OTO catalyst has a silica-to-alumina ratio, SAR, of at least 60, preferably at least 80. More preferred MFI-type zeolite has a silica-to-alumina ratio, SAR, in the range of 60 to 150, preferably in the range of 80 to 100.

The catalyst may further comprise phosphorus as such or in a compound, i.e. phosphorus other than any phosphorus included in the framework of the molecular sieve. It is preferred that a MEL or MFI-type zeolite comprising catalyst additionally comprises phosphorus.

As mention above herein above, an olefinic co-feed may be provided together with or as part of the oxygenate feedstock to the OTO process. In particular zeolite comprising catalyst, more particular MEL or MFI type zeolite comprising catalyst may convert C4 and C5 olefins in such olefinic co-feed to further ethylene and propylene. Preferably, at least part of the DME-comprising C4-C5 olefinic product is provided to the oxygenate to olefin process in step (a) together with or as part of the oxygenate-comprising feedstock as an olefinic co-feed. This way the DME removed from the reaction product is used as a feedstock to produce further ethylene and propylene. More preferably, this is done where the catalyst in the OTO process is a MEL or MFI type zeolite comprising catalyst.

The reaction conditions of the oxygenate conversion, include a reaction temperature of 350 to 1000° C., preferably from 350 to 750° C., more preferably 450 to 700° C., even more preferably 500 to 650° C.; and a pressure from 0.1 kPa (1 mbara) to 5 MPa (50 bara), preferably from 100 kPa (1 bara) to 1.5 MPa (15 bara).

Preferably, the oxygenate feedstock is preheated to a temperature in the range of from 200 to 550° C., more preferably 250 to 500° C. prior to contacting with the molecular sieve-comprising catalyst.

Where herein it is mentioned that the reaction product is obtained by converting an oxygenate-comprising feedstock in an oxygenate to olefin process, the reaction product may have also been obtained by a combination of converting an oxygenate-comprising feedstock in an oxygenate to olefin process and converting a paraffinic feedstock in a steam cracking process and combing at least part of the effluent of the oxygenate to olefin process and the stream cracking process to provide the reaction product.

EXAMPLE

The present invention is illustrated by the following non-limiting calculated examples.

The extractive distillation removal of DME from a DME-containing OTO reaction product stream was modelled using a tert-butanol solvent or a methanol solvent (not according to the invention) using Aspen V7.3 with an in-house version of the PSRK-UNIFAC property method to describe the thermodynamic behaviour of the system.

The modelled set-up includes a de-propaniser consisting of a high-pressure column section with a condenser and a low-pressure column section with a reboiler. The liquid solvent is added to the high pressure column section of the de-propaniser. As such the de-propaniser is unitised as an extractive distillation unit. The distillate retrieved from the high-pressure column is treated in a separate solvent removal column. The extractive distillation set-up as used in the model calculation is shown in FIG. 2.

Figure 2:
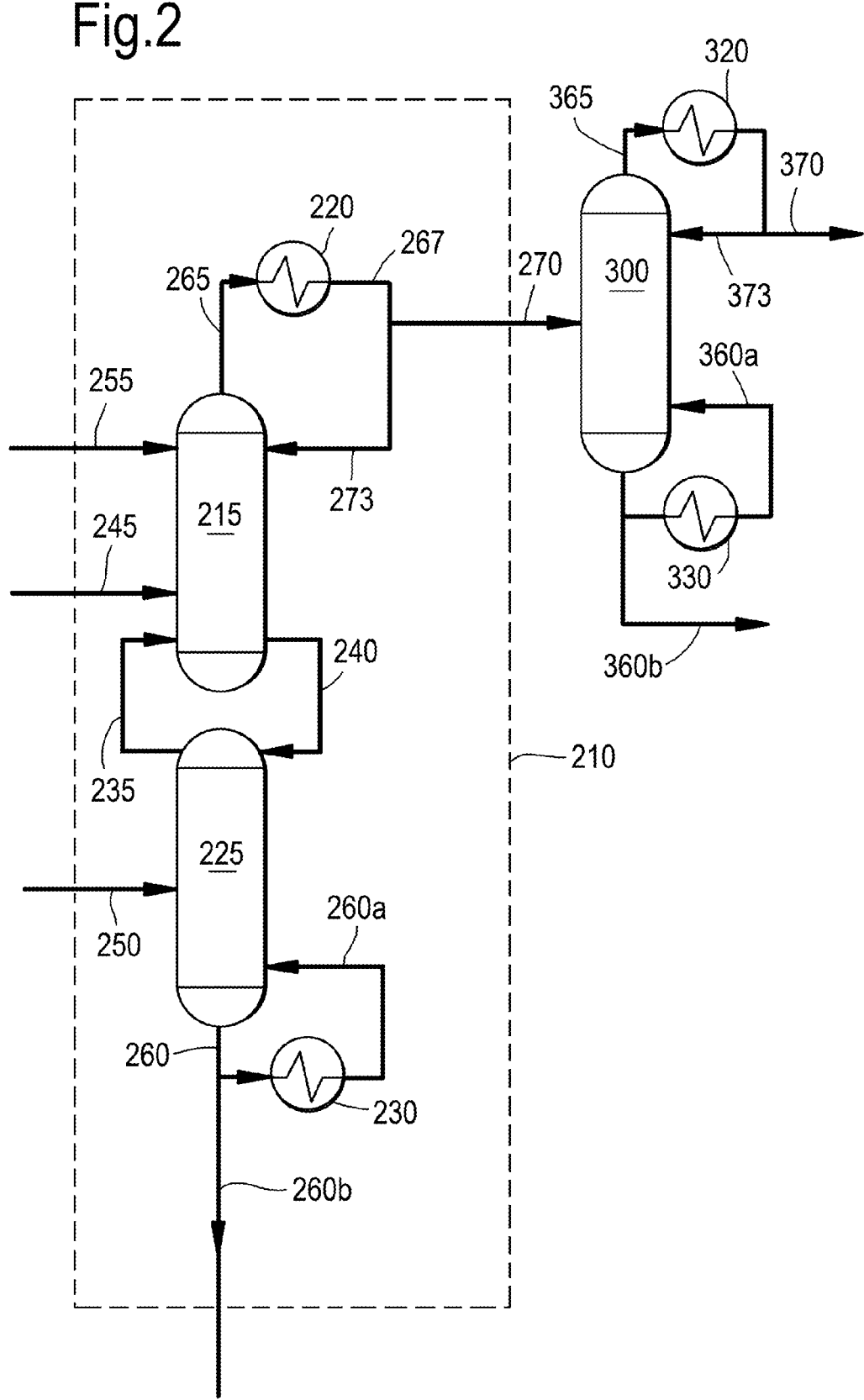
FIG. 2. depicts a diagrammatic scheme of an extractive distillation column set up.

In FIG. 2, there is shown de-propaniser 210 consisting of high-pressure column section 215 with condenser 220 and low-pressure column section 225 with reboiler 230. The top stream of low-pressure column section 225 is provided, while being condensed and pressurised (not shown), to high-pressure column section 215 via means 235, while the liquid bottom steam of high-pressure column section 215 flows to low-pressure column section 225 via means 240. OTO reaction product 245 is provided to high-pressure column section 215. Reaction product 245 may for instance have been treated in a de-ethaniser column to separate the C2− fraction from the reaction product. A second feed stream 250 is provided to low-pressure column section 225. This second feed stream may for instance be obtained from the compression section where reaction product 245 is compressed in one or more stages of a compressor train or the compression section. In the final stages of the compression of the reaction product, a liquid hydrocarbon stream condenses out from the olefin stream. This condensate is subsequently stripped in a condensate stripper to remove any entrained C3 and lighter hydrocarbons. These C3 and lighter hydrocarbons are provided to de-propaniser 210.

Solvent stream 255 is provided close to the top of high-pressure section 215 of depropaniser 210. Of second fraction 260 exiting the bottom of low-pressure column section 225, part 260a is passed to reboiler 230 and returned to low-pressure column section 225. Another part 260b of second fraction 260 is removed and further treated (not shown) to for instance recover the C4+ hydrocarbons and the solvent. First fraction 265 exiting the top of high-pressure column section 215, is passed to condenser 220. Condensed first fraction 267 is split, with one part condensed first fraction 270 being passed to separate solvent removal column 300, while another part condensed first fraction 273 is recycled to high-pressure column section 215.

Solvent removal column 300 is equipped with condenser 320 and reboiler 330. Of third fraction 360 exiting the bottom of solvent removal column 300, part 360a is passed to reboiler 330 and returned to solvent removal column 300. Another part 360b is removed and further used (not shown). Vapor fraction 365 exiting the top of solvent removal column 300, is passed to condenser 320. Condensed stream 370 is retrieved as C3− olefinic product, while part of condensed stream 370 is recycled as stream 373 to solvent removal column 300.

In the model calculations reboiler duty of reboiler 330 and distillate flow rate (condensed stream 270) were varied to achieve a fixed C4 loss, as part of the distillate of de-propaniser 210, of 0,0005 kmol/h and a fixed recovery of 95 mol % of propylene in the distillate of de-propaniser 210, based on the propylene in the total feed to de-propaniser 210. These values are typically aimed for in normal depropaniser operation.

The feed to de-propaniser 210, i.e. OTO reaction product 245 and second feed stream 250, is shown in Table 1.

TABLE 1

|  |  | Reaction product (45) | Second feed stream (50) |
| --- | --- | --- | --- |
| Temperature | ° C. | 70 | 74 |
| Pressure | barg | 23.2 | 15.6 |
| Mass flow | kg/h | 69915 | 44596 |
| Mole flow | kmol/s | 0.43 | 0.23 |
| Component |  | mol % | mol % |
| C2— |  | 0.07% | 0.02% |
| total C3 |  | 78% | 33% |
| mole fraction C3= in total C3 |  | 0.94 | 0.89 |
| total C4 |  | 20% | 45% |
| total C5 |  | 2% | 15% |
| total C6 |  | 0% | 4% |
| DME |  | 0.08% | 0.07% |

The described model is used to model DME extraction using a solvent consisting of methanol (not according to the invention) and a solvent consisting of tert-butanol, whereby the aim is to reduce the DME concentration in the condensed first fraction (270) to approximately 50 ppm (mole). Table 2 shows the composition of the condensed first fraction (270) and the solvent removal column (300) reboiler (330) duty required to remove the carried over solvent from the final C3− olefinic product. As can be seen from Table 2, it is possible to reach a 50 ppm (mole) DME concentration in the condensed first fraction (270). The required methanol flow rates to de-propaniser (210) are lower than that of tert-butanol, however due to the high tendency of the methanol to carry over into the condensed first fraction (270), the condensed first fraction (270) becomes rich in methanol, which is difficult to remove due to its similar boiling point to propylene at low concentrations. Although, at first sight condensed first fraction (270) contains similar amounts of methanol compared to tert-butanol on a mass basis, on a mole basis condensed first fraction (270) comprises 2.0 times more methanol compared to the tertbutanol solvent. As mentioned before, methanol is difficult to remove from the propylene in the condensed first fraction (270). This is seen when calculating the reboiler (330) duty required to remove the solvent from condensed first fraction (270) in the solvent removal column (300) to obtained the desired oxygenate-depleted olefin product. As can be seen from Table 2, the use of a tert-butanol solvent decreases the required reboiler (330) duty in the solvent removal column (300) by as much as 55% for the same DME removal efficiency, compared to methanol. These reductions in reboiler duty are attributed to the higher boiling temperatures of tert-butanol even at low concentration in non-polar hydrocarbon environment.

TABLE 2

| Condensed first fraction (270) | | MeOH* | t.-BuOH |
|---|---|---|---|
| DME# | ppmv | 50 | 50 |
| Solvent content# | wt % | 7 | 8 |
| reboiler (130) duty | MW | 13.5 | 6.0 |

*not according to the invention
based C3 content in condensed first fraction (270)

What is claimed is:

1. A process for producing an olefinic product, comprising:
   a) preparing a reaction product by converting an oxygenate-comprising feedstock in an oxygenate to olefin process, the reaction product comprising at least C2+ olefins and dimethylether (DME);
   b) separating at least part of the reaction product by means of extractive distillation using a butanol solvent into:
      a first fraction comprising C3− olefins and butanol; and
      a second fraction comprising C4+ olefins, dimethylether and butanol;
   c) separating the first fraction into:
      a C3− olefinic product; and
      a third fraction comprising butanol; and
   d) separating the second fraction into:
      a dimethylether-comprising C4-C5 olefinic product; and
      a fourth fraction comprising butanol and C6+ lefins,
   wherein at least part of the third and/or fourth fraction are recycled to step (b) together with or as part of the butanol solvent.

2. The process of claim 1, wherein at least part of the fourth fraction is separated into:
   a C7+ olefinic product; and
   a fifth fraction comprising C6 olefins and butanol,
   wherein at least part of the fifth fraction is recycled to step (b) together with or as part of the butanol solvent.

3. The process of claim 2, wherein the fifth fraction is separated into:
   a sixth fraction comprising butanol; and
   a seventh fraction comprising C6 olefins and butanol,
   wherein at least part of the sixth fraction is recycled to step (b) together with or as part of the butanol solvent.

4. The process of claim 1, wherein the dimethylether—comprising C4-5 olefinic product comprises isobutene and at least part of the butanol solvent is produced by converting such isobutene with water to tert-butanol.

5. The process of claim 1, wherein the butanol is tert-butanol.

6. The process of claim 1, wherein butanol solvent comprises isobutanol and/or tert-butanol.

7. The process of claim 1, wherein the reaction product comprising at least C2+ olefins and dimethylether of step (a) is separated into a C2− fraction, comprising one or more of ethane and ethylene, a C3+ reaction product and the C3+ reaction product is provided to step (b).

8. The process of claim 1, wherein the oxygenate to olefin process comprises contacting the oxygenate-comprising feedstock with a molecular sieve catalyst at a temperature in the range of from 350 to 750° C.

9. The process of claim 8, wherein the molecular sieve catalyst comprises a MEL or MFI zeolite.

10. The process of claim 9, wherein at least part of the dimethylether -comprising C4-C5 olefinic product is provided to the oxygenate to olefin process in step (a) together with or as part of the oxygenate-comprising feedstock.

11. The process of claim 9, wherein at least part of the seventh fraction comprising C6 olefins and butanol is provided to the oxygenate to olefin process in step (a) together with or as part of the oxygenate-comprising feedstock.

12. The process of claim 1, wherein the reaction product comprises at least propylene.

* * * * *